US009918683B2

(12) United States Patent
Van Arendonk

(10) Patent No.: US 9,918,683 B2
(45) Date of Patent: Mar. 20, 2018

(54) BONDING METHOD WITH CURING BY REFLECTED ACTINIC RAYS

(71) Applicant: TELEDYNE DALSA, INC., Waterloo (CA)

(72) Inventor: Anton Petrus Maria Van Arendonk, Waterloo (CA)

(73) Assignee: TELEDYNE DALSA, INC. (CA)

( * ) Notice: Subject to any disclaimer, the term of this patent is extended or adjusted under 35 U.S.C. 154(b) by 0 days.

(21) Appl. No.: 15/317,056

(22) PCT Filed: Jul. 25, 2014

(86) PCT No.: PCT/CA2014/000585
§ 371 (c)(1),
(2) Date: Dec. 7, 2016

(87) PCT Pub. No.: WO2016/011523
PCT Pub. Date: Jan. 28, 2016

(65) Prior Publication Data
US 2017/0119326 A1 May 4, 2017

(51) Int. Cl.
*G01T 1/24* (2006.01)
*A61B 6/00* (2006.01)
*G01T 7/00* (2006.01)
*F16B 11/00* (2006.01)
*H01L 27/146* (2006.01)
*H01L 31/08* (2006.01)

(52) U.S. Cl.
CPC .......... *A61B 6/4291* (2013.01); *F16B 11/006* (2013.01); *G01T 1/24* (2013.01); *G01T 7/00* (2013.01); *H01L 27/14618* (2013.01); *H01L 27/14658* (2013.01); *H01L 27/14683* (2013.01); *H01L 31/085* (2013.01)

(58) Field of Classification Search
CPC ......... H01L 27/14683; H01L 27/14663; H01L 27/14618; H01L 27/14634; H01L 27/14643; H01L 27/14658; H01L 31/0203; H01L 31/085; H01L 31/173; G01J 3/0256; A61B 6/4291; F16B 11/006
USPC .................................................... 250/370.01
See application file for complete search history.

(56) References Cited

U.S. PATENT DOCUMENTS

| 5,970,319 A | * | 10/1999 | Banks | ................... H01L 21/486 257/E21.503 |
| 8,614,421 B2 | | 12/2013 | Van Arendonk et al. | |
| 2004/0211910 A1 | * | 10/2004 | Izumi | .................. G02F 1/13336 250/370.11 |

(Continued)

OTHER PUBLICATIONS

International Search Report issued in PCT/CA2014/000585.

*Primary Examiner* — Taeho Jo
(74) *Attorney, Agent, or Firm* — McGuireWoods LLP

(57) ABSTRACT

A method of making a device having a component with a planar surface bonded to a supporting frame with openings therein by an adhesive layer cured by actinic rays, wherein part of the adhesive layer lies in the shadow of opaque portions of the supporting frame, involves bringing the component and supporting frame together with a layer of adhesive applied between them. The part of the adhesive layer in the shadow of the opaque portions is cured by directing actinic rays obliquely through the openings so that they are reflected internally into the part of the adhesive layer in the shadow of the opaque portions.

19 Claims, 1 Drawing Sheet

(56) References Cited

U.S. PATENT DOCUMENTS

| | | | | |
|---|---|---|---|---|
| 2004/0221951 A1* | 11/2004 | Chuang | ................ | H05K 3/0052 |
| | | | | 156/272.8 |
| 2006/0239605 A1* | 10/2006 | Palen | ................... | G02B 6/4206 |
| | | | | 385/14 |
| 2012/0228512 A1* | 9/2012 | van Arendonk | ...... | G01T 1/2018 |
| | | | | 250/368 |
| 2012/0306098 A1* | 12/2012 | Liou | ................. | H01L 21/02348 |
| | | | | 257/774 |
| 2017/0329023 A1* | 11/2017 | Homma | ................ | G01T 1/2018 |

* cited by examiner

BONDING METHOD WITH CURING BY REFLECTED ACTINIC RAYS

CROSS-REFERENCE TO RELATED APPLICATIONS

This application is the national stage application of and claims priority to International Patent Application No. PCT/CA2014/000585 filed on Jul. 25, 2014, the disclosure of which is incorporated by reference herein in its entirety.

FIELD OF THE INVENTION

This invention relates to the manufacture of integrated devices with planar components bonded together by an adhesive layer, and in particular but not exclusively to integrated X-ray detectors.

BACKGROUND OF THE INVENTION

In the manufacture of large medical X-ray detectors many challenges have to be overcome. In large medical X-ray detectors, materials with different thermal expansion coefficients (TCEs) need to be joined with an adhesive with a low modulus of elasticity to ensure the long-term reliability of the detector. Ultra-violet cured adhesives generally meet the requirements of low elastic modulus and low glass transition temperature. The use of a room-temperature process instead of the alternative, which is to use thermal curing, also limits the build up of mechanical stress and reduces manufacturing throughput time.

A substrate must be bonded onto a supporting frame by an adhesive layer, which is cured by the application of ultra-violet light. The supporting frame is typically in the form of a grid with openings between the grid members. The substrate is opaque to ultraviolet light, so the ultraviolet light has to be applied through openings in the frame. While the adhesive is exposed in the openings between the grid members, the latter mask the light creating a part of the adhesive layer that lies in the shadow of the grid members. As a result this part remains uncured at least only partly cured.

SUMMARY OF THE INVENTION

Embodiments of the invention address the above problem by directing actinic rays in the form of ultraviolet light into the adhesive layer at an oblique angle so that it is reflected internally into the part of the adhesive layer lying in the shadow of the grid members. In a specific application an optical stack of an X-ray detector that is not transparent to UV light is joined to a metal frame by an ultraviolet light curable adhesive to obtain the required mechanical strength.

According to the present invention there is provided a method of making an integrated device having a component with a planar surface bonded to a supporting frame with openings therein by an adhesive layer cured by actinic rays, wherein part of the adhesive layer lies in the shadow of opaque portions of the supporting frame, comprising bringing the component and supporting frame together with a layer of adhesive applied between them; and curing the part of the adhesive layer in the shadow of the opaque portions by directing actinic rays obliquely through the openings so that they are reflected internally into the part of the adhesive layer in the shadow of the opaque portions.

The integrated device may, for example, be an X-ray detector, in which case the component with a planar surface is an opaque substrate. The actinic rays may be reflected off the planar surface of the substrate.

The actinic rays may be generated by an extended ultraviolet source providing the incident light at a suitable oblique angle.

According to another aspect of the invention there is provided an integrated device comprising a component with a planar surface bonded to a supporting frame with openings therein by an adhesive layer cured by actinic rays, wherein part of the adhesive layer lies in the shadow of opaque portions of the supporting frame; and wherein the part of the part of the adhesive layer in the shadow of the opaque portions is cured by actinic rays reflected within the device.

BRIEF DESCRIPTION OF THE DRAWINGS

The invention will now be described in more detail, by way of example only, with reference to the accompanying drawings, in which.

DESCRIPTION OF EMBODIMENTS OF THE INVENTION

Figure 1:
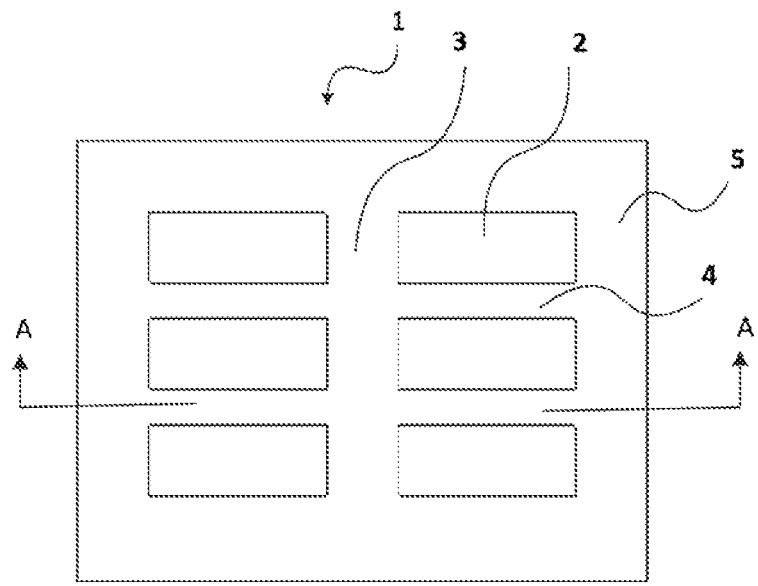
FIG. 1 is a bottom view of a support frame for a sub-assembly of an integrated device.
Figure 2:
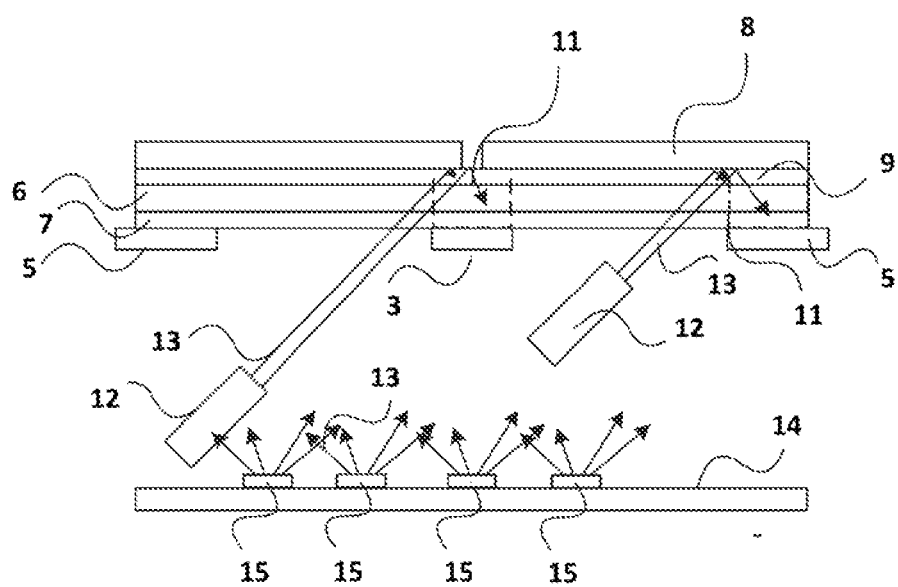
FIG. 2 is a section along the line A-A in FIG. 1.

FIG. 1 shows a generally planar aluminum support frame 1 for a large X-ray detector. The support frame 1 is of unitary construction and comprises a metal grid of orthogonal grid members 3, 4 defining rectangular openings 2 in the support frame 1 surrounded by a marginal portion 5. The support frame 1 provides the required mechanical strength for the device.

A glass carrier 6 is glued onto the support frame 1 by means of a layer of adhesive layer 7, which in this example is an epoxy adhesive, that needs curing by exposure to actinic rays in the form of ultraviolet light. An example of such an adhesive is EPO-TEK OG116-31.

A non-transparent silicon substrate 8 forming part of the optical stack is glued on top of the glass carrier layer 6 by means of an adhesive layer 9, preferably also an epoxy adhesive, which is also curable by exposure to actinic rays in the form of ultraviolet light at very high energy levels. The layer of epoxy adhesive is typically 80-150 microns thick.

An FOS/FOP fiber optic scintillator layer (not shown) is glued on top of the non-transparent silicon substrate 8 by another adhesive layer (not shown). This latter adhesive layer is a thermally curable adhesive.

Since the silicon substrate 8 is non transparent to ultraviolet light, the ultraviolet light must be launched into the sub-assembly after application of the adhesive layers through the openings 2 in the support frame 1. The problem is that the grid members 3, 4, mask the overlying parts of the adhesive layers. The grid members of the support frame 1 create shadows 11 within the adhesive layers. In one example the size of shadows is about 20 mm in the horizontal direction.

These shadows 11 prevent the uncured adhesive from receiving an adequate exposure, and as a result the adhesive may be improperly cured.

In order to overcome this problem, ultraviolet light, which in the illustrated non-limiting example, is collimated, is directed obliquely into the sub-assembly from collimated sources 12 as shown by arrows 13. The rays are reflected off the surface of the opaque silicon substrate 8 into the shadow regions of the adhesive layers 7, 9, although they could also be reflected from other interfaces within the stack by total internal reflection. The parts of the layer 7 within the shadow region 11 the benefit the most from the reflected rays since they are the regions that are the most masked by the grid members 3 of the frame.

Using this technique, lateral curing can be achieved, the amount of which depends on the thickness of the glass carrier. Up to 19 mm lateral curing was observed with the glass carrier using a glass carrier thickness of 2 mm, but this can be increased by increasing the thickness of the glass carrier 6.

Alternatively, instead of the collimated sources 12, an extended source 14, such as a flatbed source containing multiple sources 15 can be employed to ensure that the ultraviolet light is reflected back into the shadow regions.

The invention claimed is:

1. A method of making an integrated device having a component with a planar surface bonded to a supporting frame with openings therein by an adhesive layer cured by actinic rays, wherein part of the adhesive layer lies in the shadow of opaque portions of the supporting frame, comprising:
bringing the component and the supporting frame together with a layer of adhesive applied between them; and
curing the part of the adhesive layer in the shadow of the opaque portions by directing actinic rays obliquely through the openings so that they are reflected internally into the part of the adhesive layer in the shadow of the opaque portions.

2. The method as claimed in claim 1, wherein the component with a planar surface comprises a glass carrier.

3. The method as claimed in claim 2, wherein an opaque substrate is stacked on top of the glass carrier, and the actinic rays are reflected off the opaque substrate.

4. The method as claimed in claim 3, wherein the opaque substrate is adhered to the glass carrier by a further adhesive layer, and parts of said further adhesive layer lying in the shadow of said opaque portions are cured by actinic rays reflected off the opaque substrate.

5. The method as claimed in claim 4, wherein the supporting frame is in the form of a grid defining said openings.

6. The method as claimed in claim 1, wherein the supporting frame is in the form of a grid defining said openings.

7. The method as claimed in claim 6, wherein said openings are square.

8. The method as claimed in claim 7, wherein the actinic rays are ultraviolet rays.

9. The method as claimed in claim 1, wherein the actinic rays are ultraviolet rays.

10. The method as claimed in claim 9, wherein the adhesive layer is an epoxy adhesive layer.

11. The method as claimed in claim 1, wherein the adhesive layer is an epoxy adhesive layer.

12. The method as claimed in claim 11, wherein said device forms part of an X-ray detector.

13. The method as claimed claim 1, wherein said device forms part of an X-ray detector.

14. An integrated device comprising:
a component with a planar surface bonded to a supporting frame with openings therein by an adhesive layer cured by actinic rays, wherein part of the adhesive layer lies in the shadow of opaque portions of the supporting frame; and
wherein the part of the part of the adhesive layer in the shadow of the opaque portions is cured by actinic rays reflected internally within the device.

15. The device as claimed in claim 14, wherein the supporting frame is in the form of a grid defining said openings.

16. The device as claimed in claim 15, wherein said openings are square.

17. The device as claimed in claim 14, which is an X-ray detector.

18. The device as claimed in claim 14, wherein the actinic rays are ultraviolet rays.

19. The device as claimed in claim 14, wherein the adhesive layer is an epoxy adhesive layer.

* * * * *